US007689282B2

(12) United States Patent
Zhang et al.

(10) Patent No.: US 7,689,282 B2
(45) Date of Patent: Mar. 30, 2010

(54) METHOD AND APPARATUS FOR DETECTING NON-SUSTAINING VENTRICULAR TACHYARRHYTHMIA

(75) Inventors: Yunlong Zhang, Mounds View, MN (US); Jaeho Kim, Redmond, WA (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 955 days.

(21) Appl. No.: 11/424,743

(22) Filed: Jun. 16, 2006

(65) Prior Publication Data

US 2007/0293894 A1 Dec. 20, 2007

(51) Int. Cl.
*A61N 1/36* (2006.01)
(52) U.S. Cl. .................. 607/14; 600/515; 600/518; 600/519
(58) Field of Classification Search .............. 607/14; 600/515, 518, 519
See application file for complete search history.

(56) References Cited

U.S. PATENT DOCUMENTS

| 5,486,199 | A | 1/1996 | Kim et al. | |
|---|---|---|---|---|
| 5,554,175 | A | 9/1996 | Alferness | |
| 6,018,681 | A | 1/2000 | Kim | |
| 6,292,696 | B1 * | 9/2001 | Warren | 607/14 |
| 6,317,632 | B1 * | 11/2001 | Krig et al. | 607/14 |
| 6,393,321 | B2 * | 5/2002 | Warren | 607/14 |
| 6,438,418 | B1 | 8/2002 | Swerdlow et al. | |
| 6,671,548 | B1 * | 12/2003 | Mouchawar et al. | 607/14 |
| 6,961,614 | B2 | 11/2005 | Kaye | |
| 7,113,824 | B2 * | 9/2006 | Krig et al. | 607/14 |
| 2001/0021863 | A1 * | 9/2001 | Warren | 607/14 |
| 2002/0107552 | A1 * | 8/2002 | Krig et al. | 607/14 |
| 2004/0064062 | A1 * | 4/2004 | Zhou et al. | 600/515 |
| 2005/0149135 | A1 * | 7/2005 | Krig et al. | 607/14 |
| 2005/0256413 | A1 | 11/2005 | Astrom et al. | |
| 2005/0256544 | A1 | 11/2005 | Thompson | |
| 2006/0161069 | A1 | 7/2006 | Li | |

OTHER PUBLICATIONS

Denes, P., et al., "Prevalence, Characteristics and Significance of Ventricular Premature Complexes and Ventricular Tachycardia Detected by 24-Hour Continuous Electrocardiographic Recording in the Cardiac Arrhythmia Suppression Trial", *The American Journal of Cardiology*, 68(9), (1999), 887-896.

(Continued)

*Primary Examiner*—Carl H Layno
*Assistant Examiner*—Yun Haeng Lee
(74) *Attorney, Agent, or Firm*—Schwegman, Lundberg & Woessner, P.A.

(57) ABSTRACT

An implantable medical device controls an anti-tachyarrhythmia therapy by detecting a tachyarrhythmia episode from a cardiac signal and analyzing the detected tachyarrhythmia episode in a tachyarrhythmia detection and analysis process to determine whether the anti-tachyarrhythmia therapy needs to be delivered. The tachyarrhythmia detection and classification process includes detection of inhibitory events each indicating that the tachyarrhythmia episode is of a type not to be treated by the anti-tachyarrhythmia therapy or that the tachyarrhythmia episode is not sustaining. The detection of each of the inhibitory events causes the tachyarrhythmia detection and classification process to be restarted or extended, or the delivery of the anti-tachyarrhythmia therapy to be withheld.

34 Claims, 8 Drawing Sheets

OTHER PUBLICATIONS

Kapoor, W. N., et al., "Prolonged Electrocardiographic Monitoring in Patients with Syncope. Importance of Frequent or Repetitive Ventricular Ectopy.", *American Journal of Medicine*, 82(1), (1987), 20-28.

Mohiuddin, S. M., et al., "Long-Term Antiarrhythmic Therapy With Cibenzoline.", *Journal of Clinical Pharmacology*, 27(5), (1987), 400-406.

Mostow, N. D., et al., "Amiodarone: Correlation of Serum Concentration with Suppression of Complex Ventricular Ectopic Activity", *The American Journal of Cardiology*, 54(6), (1984), 569-574.

Nademanee, K., et al., "Electrophysiologic and Antiarrhythmic Effects of Sotalol in Patients with Life-Threatening Ventricular Tachyarrhythmias", *Circulation*, 72(3), (1985), 555-564.

Olsson, G., et al., "Ventricular Arrhythmias During the First Year After Acute Myocardial Infarction: Influence of Long-Term Treatment with Metoprolol.", *Circulation*, 69(6), (1984), 1129-1134.

Rehnqvist, N., et al., "Comparative Study of Tocainide and Lidocaine in Patients Admitted for Suspected Acute Myocardial Infarction.", *Acta Medica Scandinavica*, 214(1), (1983), 21-27.

* cited by examiner

| BEAT NO. | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 | 25 | 26 | 27 | 28 | 29 | 30 | 31 | 32 |
|---|---|---|---|---|---|---|---|---|---|---|---|---|---|---|---|---|---|---|---|---|---|---|---|---|---|---|---|---|---|---|---|---|
| P.I | F | F | F | S | F | F | F | S | F | F | F | S | F | F | S | F | F | S | F | F | S | F | F | S | F | F | S | F | F | S | F | F |
| P.II | F | F | F | F | S | S | F | F | F | F | S | S | F | F | S | F | F | S | F | F | S | F | F | S | F | F | S | F | F | S | F | F |
| P.III | F | F | F | F | F | F | F | F | S | S | S | F | F | F | S | F | F | F | S | F | F | F | S | F | F | F | S | F | F | F | S | F |
| P.IV | F | F | F | F | F | F | F | F | S | S | S | S | F | F | F | F | F | F | S | S | S | S | F | F | F | F | F | F | S | S | S | S |

*Fig.6*

METHOD AND APPARATUS FOR DETECTING NON-SUSTAINING VENTRICULAR TACHYARRHYTHMIA

TECHNICAL FIELD

This document relates generally to cardiac rhythm management (CRM) systems and particularly to such a system providing for determination of whether a detected ventricular tachyarrhythmia is sustaining.

BACKGROUND

Tachyarrhythmias are abnormal heart rhythms characterized by a rapid heart rate. Tachyarrhythmias generally include supraventricular tachyarrhythmia (SVT, including atrial tachyarrhythmia, AT) and ventricular tachyarrhythmia (VT). Fibrillation is a form of tachyarrhythmia further characterized by an irregular heart rhythm. In a normal heart, the sinoatrial node, the heart's predominant natural pacemaker, generates electrical impulses, called action potentials, that propagate through an electrical conduction system to the atria and then to the ventricles of the heart to excite the myocardial tissues. The atria and ventricles contract in the normal atrioventricular sequence and synchrony to result in efficient blood-pumping functions indicated by a normal hemodynamic performance. VT occurs when the electrical impulses propagate along a pathologically formed self-sustaining conductive loop within the ventricles or when a natural pacemaker in a ventricle usurps control of the heart rate from the sinoatrial node. When the atria and the ventricles become dissociated during VT, the ventricles may contract before they are properly filled with blood, resulting in diminished blood flow throughout the body. This condition becomes life-threatening when the brain is deprived of sufficient oxygen supply. Ventricular fibrillation (VF), in particular, stops blood flow within seconds and, if not timely and effectively treated, causes immediate death. In very few instances a heart recovers from VF without treatment.

Cardioversion and defibrillation are used to terminate most tachyarrhythmias, including AT, VT, and VF. An implantable cardioverter/defibrillator (ICD) is a cardiac rhythm management (CRM) device that delivers a cardioversion/defibrillation pulse (also known as a shock) to terminate a detected tachyarrhythmia episode by depolarizing the entire myocardium simultaneously and rendering it refractory.

Because the cardioversion/defibrillation pulse causes pain in the patient and drains a substantial amount of energy from the ICD's battery, its delivery is justified when it is necessary, such as when a life-threatening VT or VF is occurring. An unnecessary delivery of the cardioversion/defibrillation pulse causes pain and shortens the longevity of the ICD without benefiting the patient. A detection of tachyarrhythmia based on heart rate is not sufficient for determining the need and adequacy of delivering the cardioversion/defibrillation pulse. For example, a transient, non-sustaining VT may terminate itself without device intervention.

For these and other reasons, there is a need for determining whether to deliver the cardioversion/defibrillation pulse based on the nature of a detected tachyarrhythmia episode.

SUMMARY

An implantable medical device controls an anti-tachyarrhythmia therapy by detecting a tachyarrhythmia episode from a cardiac signal and analyzing the detected tachyarrhythmia episode in a tachyarrhythmia detection and analysis process to determine whether the anti-tachyarrhythmia therapy needs to be delivered. The tachyarrhythmia detection and classification process includes detection of inhibitory events each indicating that the tachyarrhythmia episode is of a type not to be treated by the anti-tachyarrhythmia therapy or that the tachyarrhythmia episode is not sustaining. The detection of each of the inhibitory events causes the tachyarrhythmia detection and classification process to be restarted or extended, or the delivery of the anti-tachyarrhythmia therapy to be withheld.

In one embodiment, an ICD includes a defibrillation circuit, a sensing circuit, and a controller. The defibrillation circuit delivers cardioversion/defibrillation pulses. The sensing circuit senses a cardiac signal. The controller includes a tachyarrhythmia detector, an inhibitory event detector, and a defibrillation controller. The tachyarrhythmia detector detects a predetermined type initiation event indicative of a tachyarrhythmia episode from the cardiac signal. In response to the detection of the predetermined type initiation event, the tachyarrhythmia detector starts a tachyarrhythmia detection and classification process. The tachyarrhythmia detection and classification process determines whether the tachyarrhythmia episode sustains and is to be treated by delivering one or more of the cardioversion/defibrillation pulses. The inhibitory event detector detects a predetermined type inhibitory event from the cardiac signal. The predetermined type inhibitory event is indicative of a need to inhibit a delivery of an anti-tachyarrhythmia therapy, such as the delivery of one or more of the cardioversion/defibrillation pulses. In response to the detection of the predetermined type inhibitory event, the tachyarrhythmia detector restarts or extends the tachyarrhythmia detection and classification process. The defibrillation controller controls the delivery of the cardioversion/defibrillation pulses.

In one embodiment, a method for operating an ICD is provided. A cardiac signal is sensed. A predetermined type initiation event indicative of a tachyarrhythmia episode is detected from the cardiac signal. A tachyarrhythmia detection and classification process is started when the predetermined type initiation event is detected. A predetermined type inhibitory event is detected from the cardiac signal. The predetermined type inhibitory event is indicative of a need to inhibit a delivery of an anti-tachyarrhythmia therapy. The tachyarrhythmia detection and classification process is restarted or extended when the predetermined type inhibitory event is detected.

This Summary is an overview of some of the teachings of the present application and not intended to be an exclusive or exhaustive treatment of the present subject matter. Further details about the present subject matter are found in the detailed description and appended claims. Other aspects of the invention will be apparent to persons skilled in the art upon reading and understanding the following detailed description and viewing the drawings that form a part thereof, each of which are not to be taken in a limiting sense. The scope of the present invention is defined by the appended claims and their legal equivalents.

BRIEF DESCRIPTION OF THE DRAWINGS

The drawings illustrate generally, by way of example, but not by way of limitation, various embodiments discussed in the present document.

FIG. 6 is an illustration of arrhythmia patterns each being an example of an inhibitory event.

DETAILED DESCRIPTION

Figure 1:
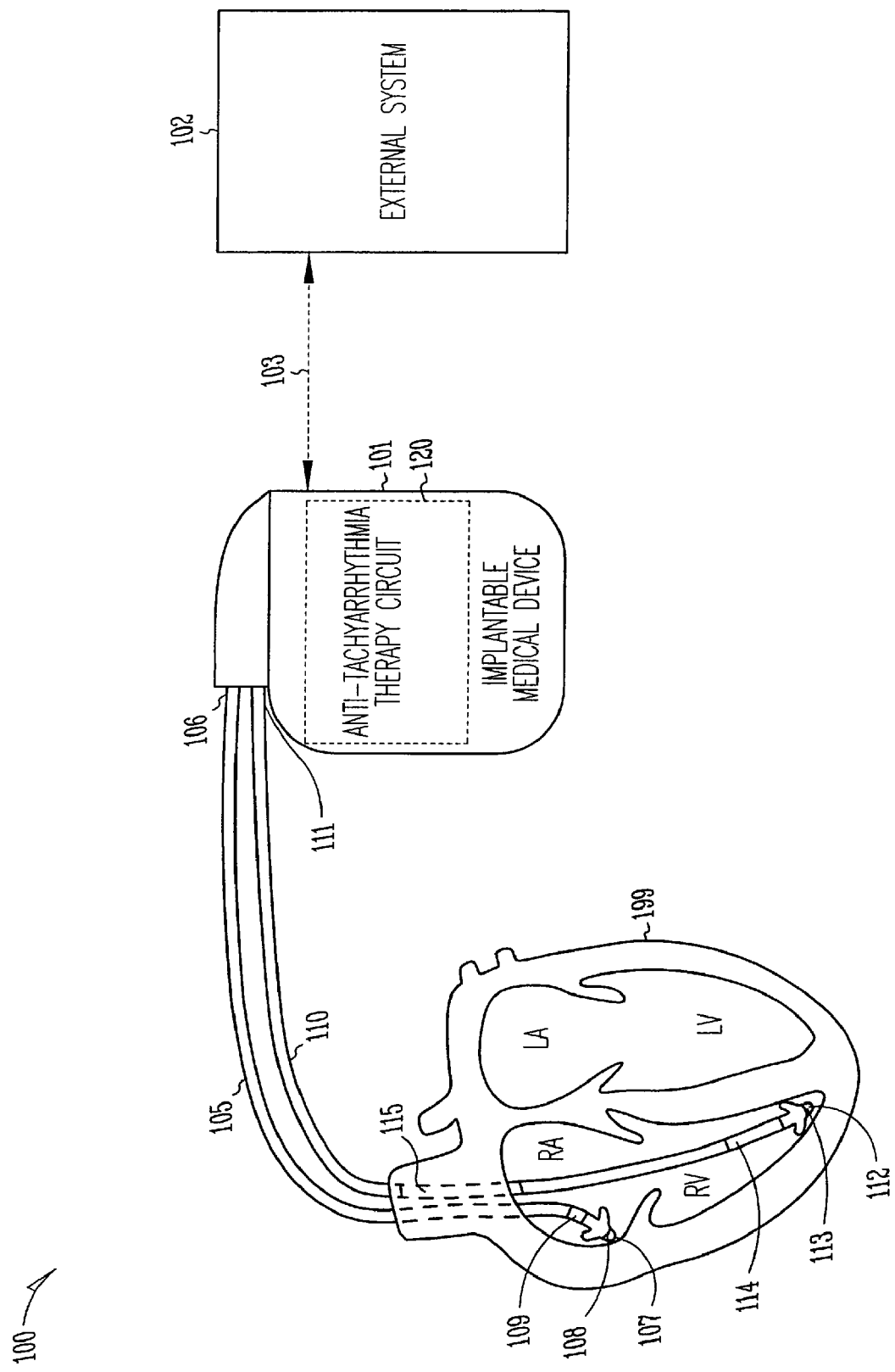
FIG. 1 is an illustration of one embodiment of a CRM system and portions of the environment in which the CRM system operates.

In the following detailed description, reference is made to the accompanying drawings which form a part hereof, and in which is shown by way of illustration specific embodiments in which the invention may be practiced. These embodiments are described in sufficient detail to enable those skilled in the art to practice the invention, and it is to be understood that the embodiments may be combined, or that other embodiments may be utilized and that structural, logical and electrical changes may be made without departing from the scope of the present invention. The following detailed description provides examples, and the scope of the present invention is defined by the appended claims and their legal equivalents.

In this document, the terms "a" or "an" are used, as is common in patent documents, to include one or more than one. In this document, the term "or" is used to refer to a nonexclusive or, unless otherwise indicated. Furthermore, all publications, patents, and patent documents referred to in this document are incorporated by reference herein in their entirety, as though individually incorporated by reference. In the event of inconsistent usages between this documents and those documents so incorporated by reference, the usage in the incorporated reference(s) should be considered supplementary to that of this document; for irreconcilable inconsistencies, the usage in this document controls.

It should be noted that references to "an", "one", or "various" embodiments in this document are not necessarily to the same embodiment, and such references contemplate more than one embodiment.

In this document, a "fast beat" refers to a heart beat having a heart rate that falls into a tachyarrhythmia detection zone, which is typically defined by at least one tachyarrhythmia detection threshold, and a "slow beat" refers to a heart beat having a heart rate that is below the tachyarrhythmia detection zone. In other words, a "fast beat" is a heart beat having a tachyarrhythmic heart rate, and a "slow beat" is a heart beat having a heart rate that is not tachyarrhythmic. A paced heart beat is typically considered as a slow beat.

This document discusses a CRM system including an implantable medical device that detects and treats tachyarrhythmia episodes. When a tachyarrhythmia episode is detected based on a fast heart rate, the tachyarrhythmia episode typically needs to be analyzed to determine whether to deliver an anti-tachyarrhythmia therapy such as a cardioversion/defibrillation therapy or an anti-tachyarrhythmia pacing (ATP) therapy. This typically includes a determination of whether the detected tachyarrhythmia episode sustains and a classification of the detected tachyarrhythmia episode by its origin and/or type.

In one example of an ICD capable of delivering ventricular cardioversion/defibrillation pulses, a detection of three consecutive fast beats from a ventricular electrogram starts a tachyarrhythmia detection and classification process. In response to the detection of three consecutive fast beats, a tachyarrhythmia detection window is started. The tachyarrhythmia detection window includes ten consecutively detected heart beats starting with and including the three consecutive fast beats. If at least eight out of the ten heart beats in the tachyarrhythmia detection window are fast beats (i.e., the tachyarrhythmia detection window is satisfied), a tachyarrhythmia verification duration is started. Otherwise, the tachyarrhythmia detection and classification process is terminated without delivering a ventricular anti-tachyarrhythmia therapy. During the tachyarrhythmia verification duration, a moving verification window of ten consecutively detected heart beats is used to determine whether the detected tachyarrhythmia sustains. If at least six out of the ten heart beats in the verification window are fast beats (i.e., the verification window is satisfied), the detected tachyarrhythmia is considered to be sustaining. If this verification window fails to be satisfied at any time during the tachyarrhythmia verification duration, the tachyarrhythmia detection and classification process is terminated without delivering a ventricular anti-tachyarrhythmia therapy. If the detected tachyarrhythmia episode is determined to be sustaining throughout the tachyarrhythmia verification duration, it is classified by its origin and/or type to determine whether a ventricular anti-tachyarrhythmia therapy will be necessary. In one embodiment, the preparation for a ventricular cardioversion/defibrillation therapy is started if the detected tachyarrhythmia episode is classified as a VT episode. After the preparation is completed, a tachyarrhythmia reconfirmation window of three consecutive heart beats is started, immediately before a scheduled ventricular cardioversion/defibrillation pulse delivery. If at least two out of the three heart beats in the tachyarrhythmia reconfirmation window are fast beats (i.e., the tachyarrhythmia reconfirmation window is satisfied), the detected tachyarrhythmia is considered to be still sustaining, and the ventricular cardioversion/defibrillation pulse is delivered. While such a tachyarrhythmia detection and classification process is effective in preventing unnecessary or ineffective ventricular cardioversion/defibrillation pulses under many circumstances, there are still scenarios in which this process is carried out correctly but results in unnecessary delivery of ventricular cardioversion/defibrillation pulses. Examples of such scenarios include frequent triplet premature ventricular contractions (PVCs) and short-run ventricular arrhythmias that display particular fast-slow beat patterns. Specific examples of such fast-slow beat patterns are further discussed below with reference to FIG. 6.

In various embodiments, the present implantable medical device detects inhibitory events during the tachyarrhythmia detection and classification process. The inhibitory events each indicate that an anti-tachyarrhythmia therapy is unnecessary and therefore to be inhibited. Examples of such inhibitory events include: (1) particular fast-slow beat patterns indicative of frequent triplet PVCs rather than VT, and (2) slow beats that are morphologically correlated to beat of normal sinus rhythm (NSR) or SVT, indicating that VT is not self-sustaining. In one embodiment, if an inhibitory event is detected during the tachyarrhythmia verification duration while the verification window is satisfied, the tachyarrhythmia detection and classification process is restarted from the tachyarrhythmia detection window. In another embodiment, if the inhibitory event is detected during the tachyarrhythmia verification duration while the verification window is satisfied, the tachyarrhythmia verification duration is extended until after the inhibitory event is no longer detected. If an inhibitory event is detected during the tachyarrhythmia reconfirmation window while the tachyarrhythmia reconfirmation window is satisfied, the tachyarrhythmia reconfirmation window is restarted or extended, and the delivery of the anti-tachyarrhythmia therapy is withheld unless and until the inhibitory event is no longer detected.

While cardioversion/defibrillation therapy is specifically discussed below as an example of anti-tachyarrhythmia therapies, the present subject matter is applicable in all anti-tachyarrhythmia therapies, including ATP, in which non-sustaining ventricular tachyarrhythmia episodes are detected to reduce or eliminate delivery of unnecessary anti-tachyarrhythmia therapies.

FIG. 1 is an illustration of an embodiment of a CRM system 100 and portions of the environment in which CRM system 100 operates. CRM system 100 includes an implantable medical device 101 that is electrically coupled to a heart 199 through one or more electrodes, such as on leads 105 and 110, or elsewhere. An external system 102 communicates with implantable medical device 101 via a telemetry link 103.

Implantable medical device 101 delivers anti-tachyarrhythmia therapies including ATP and cardioversion/defibrillation therapies. In one embodiment, implantable medical device 101 is an implantable cardioverter/defibrillator (ICD) with cardiac pacing capabilities. In another embodiment, in addition to a pacemaker and a cardioverter/defibrillator, implantable medical device 101 includes one or more of other monitoring and/or therapeutic devices such as a neural stimulator, a drug delivery device, and a biological therapy device. Implantable medical device 101 includes a hermetically sealed can housing an electronic circuit that senses physiological signals and delivers therapeutic electrical pulses. The hermetically sealed can may also function as an electrode for sensing and/or pulse delivery purposes. In one embodiment, as illustrated in FIG. 1, the electronic circuit senses at least an atrial electrogram and a ventricular electrogram from heart 199 and delivers pacing and cardioversion/defibrillation pulses to heart 199. Lead 105 is typically a pacing lead that includes a proximal end 106 connected to implantable medical device 101 and a distal end 107 placed in the right atrium (RA) of heart 199. A pacing-sensing electrode 108 (referred to as the "RA tip" electrode) is located at distal end 107. Another pacing-sensing electrode 109 (referred to as the "RA ring" electrode) is located near distal end 107. Electrodes 108 and 109 are electronically connected to implantable medical device 101 via separate conductors in lead 105 to allow sensing of the atrial electrogram and/or delivery of atrial pacing pulses. Lead 110 is typically a defibrillation lead that includes a proximal end 111 connected to implantable medical device 101 and a distal end 112 placed in the right ventricle (RV) of heart 199. A pacing-sensing electrode 113 (referred to as the "RV tip" electrode) is located at distal end 112. A defibrillation electrode 114 (referred to as the "RV coil" electrode) is located near distal end 112 but electrically separated from pacing-sensing electrode 113. Another defibrillation electrode 115 (referred to as the "SVC coil" electrode) is located at a distance from distal end 112 for placement in the superior vena cava (SVC). In one embodiment, electrode 115 is electrically connected to the hermetically sealed can. Electrodes 113, 114, and 115 are electrically connected to implantable medical device 101 via separate conductors in lead 110. Electrode 113 allows sensing of the ventricular electrogram and/or delivery of ventricular pacing pulses. Electrodes 114 and 115 allow sensing of the ventricular electrogram and/or delivery of ventricular cardioversion/defibrillation pulses.

Leads 105 and 110 are shown in FIG. 1 for illustrative purposes only. Other lead configurations may be used to sense electrograms and delivering pacing and/or cardioversion/defibrillation pulses. For example, as illustrated in FIG. 1, lead 110 includes defibrillation electrodes 114 and 115. Electrode 115 may be connected to the hermetically sealed can that houses implantable medical device 101. Ventricular cardioversion/defibrillation pulses may be delivered through electrode 114 and electrode 115 and/or the hermetically sealed can. Alternatively, lead 110 may include defibrillation electrode 114 but not defibrillation electrode 115. Ventricular cardioversion/defibrillation pulses are delivered through electrode 114 and the hermetically sealed can.

Implantable medical device 101 includes an anti-tachyarrhythmia therapy circuit 120 that delivers a cardioversion/defibrillation pulse after a detected tachyarrhythmia episode is confirmed to be sustaining and of a type for which the cardioversion/defibrillation therapy is necessary. Anti-tachyarrhythmia therapy circuit 120 detects inhibitory events during a tachyarrhythmia detection and classification process to inhibit the delivery of the cardioversion/defibrillation pulse at the end of the process. The inhibitory events each indicate that the cardioversion/defibrillation therapy is unnecessary, either because the detected tachyarrhythmia episode is not sustaining, or because the detected tachyarrhythmia episode is of a type for which the cardioversion/defibrillation therapy is not an appropriate treatment. Various embodiments of anti-tachyarrhythmia therapy circuit 120 are discussed below, with reference to FIGS. 2-5. In various embodiments, implantable medical device 101 also includes one or more of other cardiac electrical therapy circuits such as an anti-bradyarrhythmia circuit, a cardiac resynchronization therapy (CRT) circuit, a cardiac remodeling control therapy (RCT) circuit.

External system 102 allows for programming of implantable medical device 101 and receives signals acquired by implantable medical device 101. In one embodiment, external system 102 includes a programmer. In another embodiment, external system 102 is a patient management system including an external device in proximity of implantable medical device 101, a remote device in a relatively distant location, and a telecommunication network linking the external device and the remote device. The patient management system allows access to implantable medical device 101 from a remote location, such as for monitoring patient status and adjusting therapies. Telemetry link 103 is a wireless communication link providing for bidirectional data transmission between implantable medical device 101 and external system 102. In one embodiment, telemetry link 103 is an inductive telemetry link. In an alternative embodiment, telemetry link 103 is a far-field radio-frequency telemetry link. Telemetry link 103 provides for data transmission from implantable medical device 101 to external system 102. This may include, for example, transmitting real-time physiological data acquired by implantable medical device 101, extracting physiological data acquired by and stored in implantable medical device 101, extracting therapy history data stored in implantable medical device 101, and extracting data indicating an operational status of implantable medical device 101 (e.g., battery status and lead impedance). Telemetry link 103 also provides for data transmission from external system 102 to implantable medical device 101. This may include, for example, programming implantable medical device 101 to acquire physiological data, programming implantable medical device 101 to perform at least one self-diagnostic test (such as for a device operational status), programming implantable medical device 101 to enable an available monitoring or therapeutic function, and programming implantable medical device 101 to adjust therapeutic parameters such as pacing and/or cardioversion/defibrillation parameters.

Anti-tachyarrhythmia therapy circuit 120 may be implemented using a combination of hardware and software. In various embodiments, each element of anti-tachyarrhythmia therapy circuit 120, including its specific embodiments discussed in this document, may be implemented using an application-specific circuit constructed to perform one or more particular functions or a general-purpose circuit programmed to perform such function(s). Such a general-purpose circuit includes, but is not limited to, a microprocessor or a portion thereof, a microcontroller or portions thereof, and a programmable logic circuit or a portion thereof. For example, a "timer" includes, among other things, an electronic circuit timer constructed to perform the only function of timing or counting, or a general-purpose circuit driven by a code instructing that portion of the general-purpose circuit to perform the timing or counting.

Figure 2:
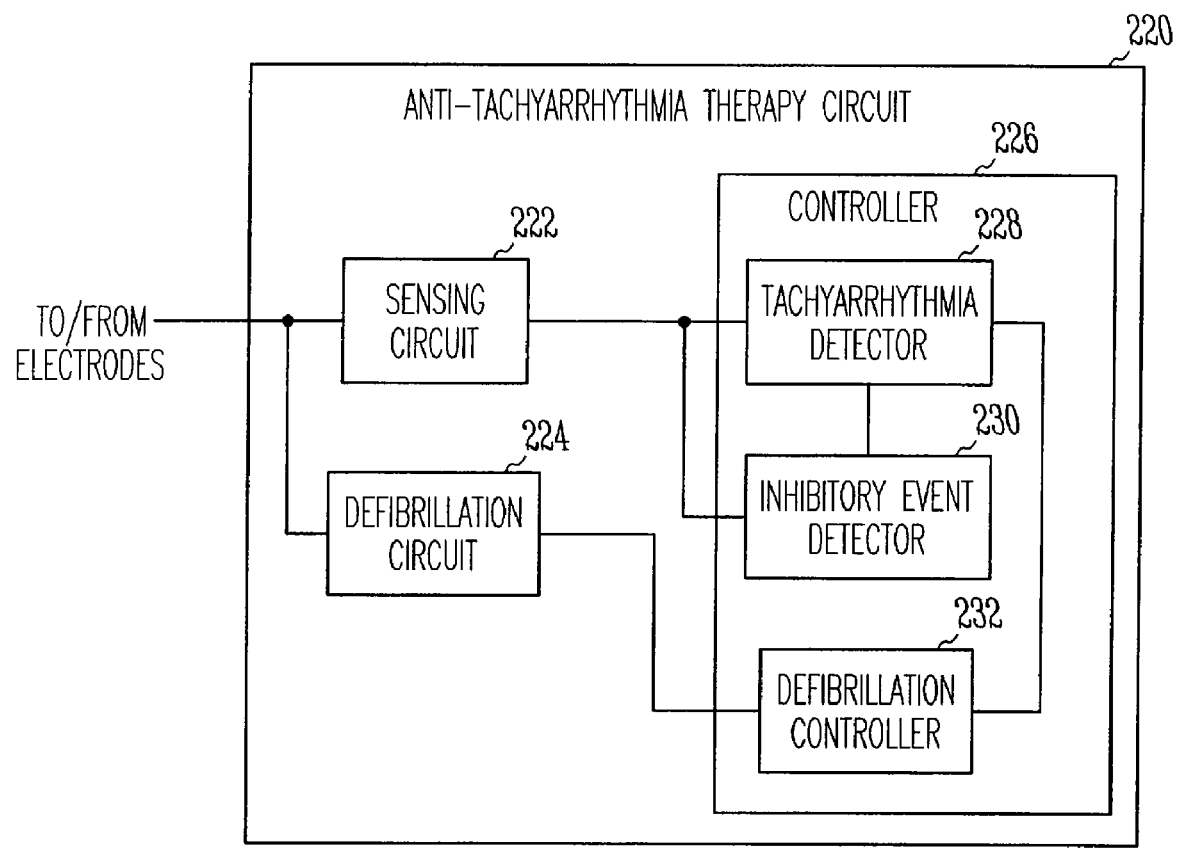
FIG. 2 is a block diagram illustrating an embodiment of an anti-tachyarrhythmia therapy circuit of an implantable medical device of the CRM system.

FIG. 2 is a block diagram illustrating an embodiment of an anti-tachyarrhythmia therapy circuit 220, which is a specific embodiment of anti-tachyarrhythmia therapy circuit 120. Anti-tachyarrhythmia therapy circuit 220 includes a sensing circuit 222, a defibrillation circuit 224, and a controller 226. Sensing circuit 222 senses a cardiac signal from the heart. Defibrillation circuit 224 delivers cardioversion/defibrillation pulses to the heart. Controller 226 includes a tachyarrhythmia detector 228, an inhibitory event detector 230, and a defibrillation controller 232. Tachyarrhythmia detector 228 detects a predetermined type initiation event indicative of a tachyarrhythmia episode from the sensed cardiac signal. In response to the detection of an initiation event, tachyarrhythmia detector 228 starts a tachyarrhythmia detection and classification process. The tachyarrhythmia detection and classification process determines whether the tachyarrhythmia episode sustains and is treatable by delivering one or more of the cardioversion/defibrillation pulses. Inhibitory event detector 230 detects a predetermined type inhibitory event from the sensed cardiac signal. The predetermined type inhibitory event indicates a need to inhibit the delivery of the cardioversion/defibrillation pulses. In response to the detection of the inhibitory event, tachyarrhythmia detector 228 restarts or extends the tachyarrhythmia detection and classification process. Defibrillation controller 232 controls the delivery of the cardioversion/defibrillation pulses based on an outcome of the tachyarrhythmia detection and classification process.

In one embodiment, in which anti-tachyarrhythmia therapy circuit 220 provides for ventricular cardioversion/defibrillation, sensing circuit 222 includes a ventricular sensing channel to sense a ventricular electrogram using a ventricular lead such as lead 110. Defibrillation circuit 224 includes a ventricular defibrillation circuit that delivers ventricular cardioversion/defibrillation pulses. Tachyarrhythmia detector 228 detects a predetermined type initiation event indicative of a VT episode from the ventricular electrogram and starts a VT detection and classification process in response to the detection of the initiation event. In one embodiment, in response to the detection of the inhibitory event, tachyarrhythmia detector 228 restarts the VT detection and classification process. In another embodiment, in response to the detection of the inhibitory event, tachyarrhythmia detector 228 extends the VT detection and classification process until after the inhibitory event is no longer detected. Defibrillation controller 232 causes the delivery of a ventricular cardioversion/defibrillation pulse if the outcome of the VT detection and classification process indicates a sustaining VT, rather than another arrhythmia such as a non-sustaining VT or a fast ventricular rhythm caused by an SVT.

Figure 3:
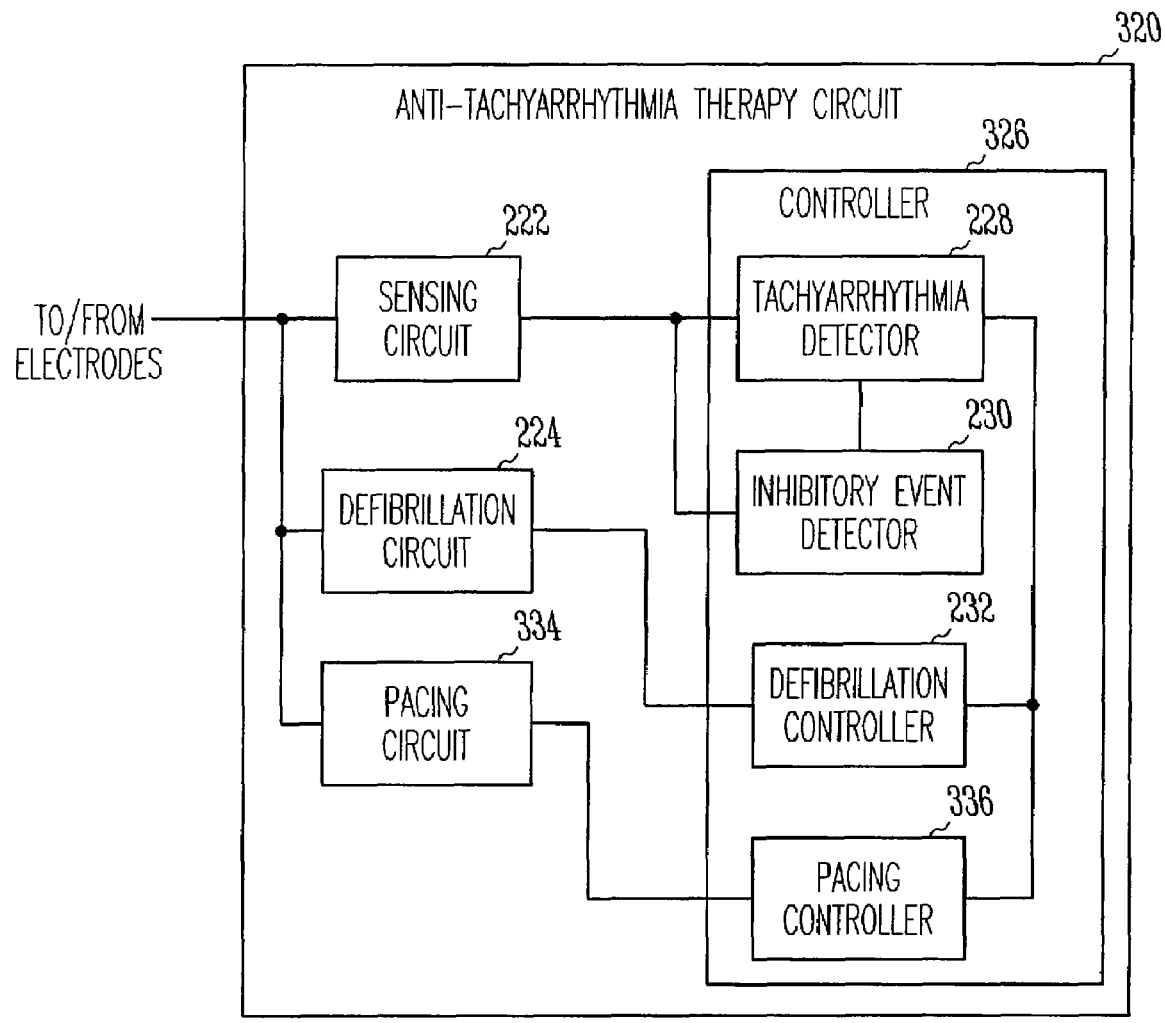
FIG. 3 is a block diagram illustrating another embodiment of the anti-tachyarrhythmia therapy circuit.

FIG. 3 is a block diagram illustrating an embodiment of an anti-tachyarrhythmia therapy circuit 320, which is another specific embodiment of anti-tachyarrhythmia therapy circuit 120. Anti-tachyarrhythmia therapy circuit 320 includes sensing circuit 222, defibrillation circuit 224, a pacing circuit 334, and a controller 326. Controller 326 includes tachyarrhythmia detector 228, inhibitory event detector 230, defibrillation controller 232, and a pacing controller 336. In addition to delivering cardioversion/defibrillation therapy, anti-tachyarrhythmia therapy circuit 320 is capable of delivering pacing therapy, including anti-tachyarrhythmia pacing (ATP) therapy. Pacing circuit 334 delivers pacing pulses to the heart. Pacing controller 336 controls the delivery of the pacing pulses. In one embodiment, pacing controller 336 controls the delivery of the pacing pulses according to an ATP algorithm, using the outcome of the tachyarrhythmia detection and classification process. In various embodiments, pacing controller 336 is also capable of controlling the delivery of the pacing pulses according to other pacing algorithms such as bradyarrhythmia pacing, CRT pacing, and RCT pacing algorithms.

Figure 4:
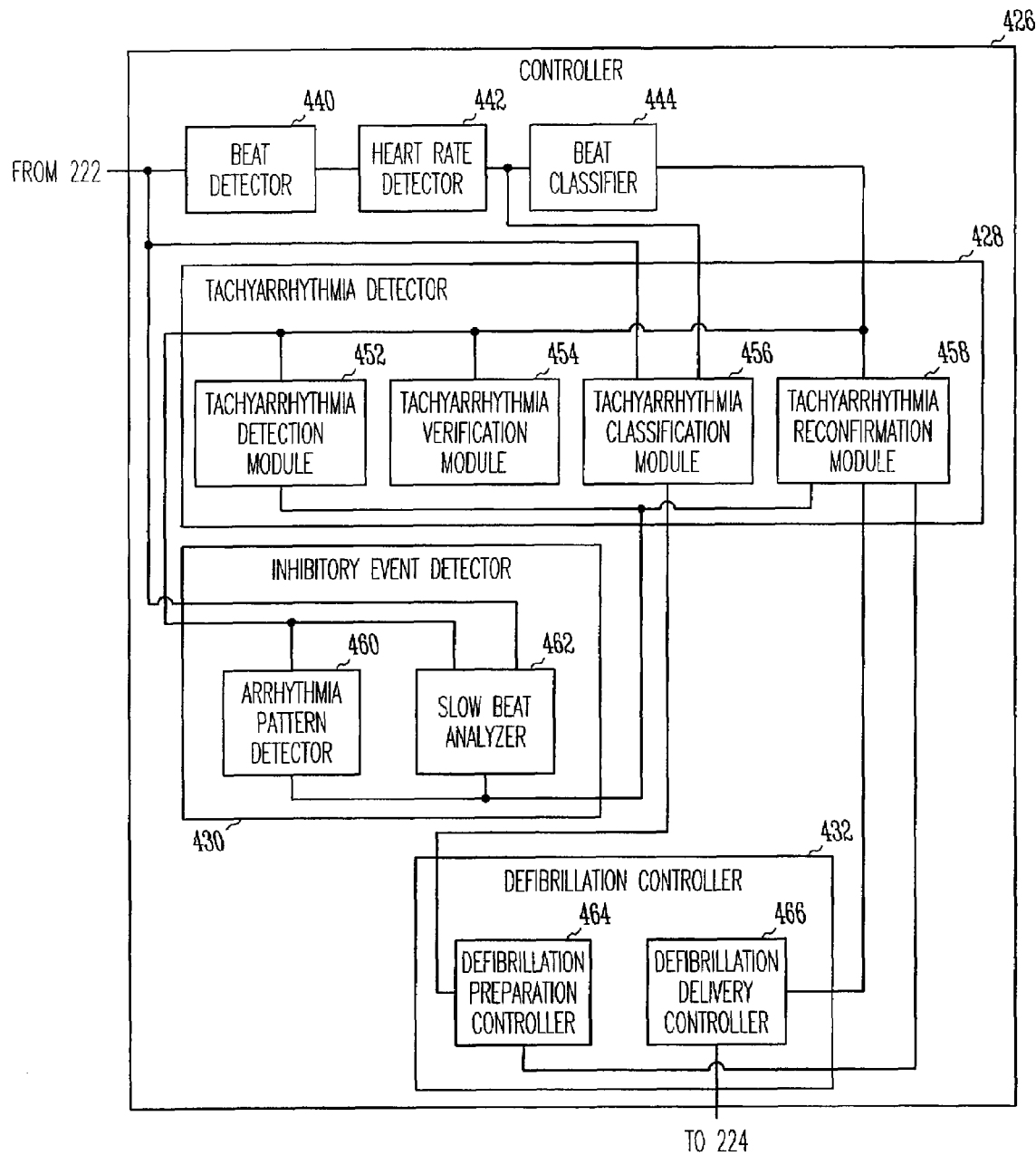
FIG. 4 is a block diagram illustrating an embodiment of a controller of the anti-tachyarrhythmia therapy circuit.

FIG. 4 is a block diagram illustrating an embodiment of a controller 426, which is a specific embodiment of controller 226. Controller 426 includes a beat detector 440, a heart rate detector 442, a beat classifier 444, a tachyarrhythmia detector 428, an inhibitory event detector 430, and a defibrillation controller 432.

Beat detector 440 detects heart beats from the cardiac signal sensed by sensing circuit 222. Heart rate detector 442 detects the heart rate of each of the detected heart beats. Beat classifier 444 classifies each of the detected heart beat as one of a fast beat and a slow beat. In one embodiment, beat classifier 444 classifies each of the detected heart beats as a fast beat if the heart rate of that heart beat exceeds a tachyarrhythmia detection threshold, and as a slow beat if the heart rate of that heart beat does not exceed the tachyarrhythmia detection threshold. If a heart beat is a paced beat, beat classifier 444 classifies it as a slow beat. In one embodiment, in which controller 426 controls ventricular cardioversion/defibrillation, beat detector 440 detects ventricular events as the heart beats from the ventricular electrogram sensed by sensing circuit 222. Rate detector 442 detects the ventricular rate of each of the detected ventricular events. Beat classifier 444 classifies each of the detected ventricular events as one of a fast beat and a slow beat. In a specific embodiment, beat classifier 444 classifies each of the detected ventricular events as a fast beat if the ventricular rate of that ventricular event exceeds a VT detection threshold, and as a slow beat if the ventricular rate of that ventricular event does not exceed the VT detection threshold. If a ventricular event is a paced ventricular event, beat classifier 444 classifies it as a slow beat.

Tachyarrhythmia detector 428 is a specific embodiment of tachyarrhythmia detector 228 and performs the tachyarrhythmia detection and classification process to determine whether a cardioversion/defibrillation therapy is to be delivered. Tachyarrhythmia detector 428 includes a tachyarrhythmia detection module 452, a tachyarrhythmia verification module 454, a tachyarrhythmia classification module 456, and a tachyarrhythmia reconfirmation module 458.

Tachyarrhythmia detection module 452 detects a predetermined type initiation event indicative of a tachyarrhythmia episode, such as a predetermined number of consecutively detected fast beats. In response to a detection of the predetermined type initiation event, tachyarrhythmia detection module 452 starts a tachyarrhythmia detection window. If the heart beats detected during the tachyarrhythmia detection window include at least a minimum number or percentage of fast beats, a detection of tachyarrhythmia is declared (the tachyarrhythmia detection window is satisfied). Otherwise, the tachyarrhythmia detection and classification process is terminated without delivering the cardioversion/defibrillation therapy.

In response to the declaration of the detection of tachyarrhythmia, tachyarrhythmia verification module 454 starts a tachyarrhythmia verification duration. If the heart beats detected during a moving verification window include at least a minimum number or percentage of fast beats throughout the tachyarrhythmia verification duration, a verification of tachyarrhythmia is declared (the tachyarrhythmia verification duration is satisfied). If the heart beats detected during a moving verification window does not include at least the minimum number or percentage of fast beats at any time during the tachyarrhythmia verification duration, the tachyarrhythmia detection and classification process is terminated without delivering the cardioversion/defibrillation therapy.

In response to the declaration of the verification of tachyarrhythmia, tachyarrhythmia classification module 456 classifies the detected tachyarrhythmia episode by its origin and/or type. In one embodiment, tachyarrhythmia classification module 456 classifies the detected tachyarrhythmia episode as one of VT and SVT by comparing the morphology of the cardiac signal sensed during the detected tachyarrhythmia episode to a template morphology associated with a known cardiac rhythm such as a normal sinus rhythm (NSR). Specific examples of tachyarrhythmia classification are discussed in U.S. patent application Ser. No. 11/038,996, entitled "METHODS AND APPARATUSES FOR CARDIAC ARRHYTHMIA CLASSIFICATION USING MORPHOLOGY STABILITY," filed on Jan. 20, 2005 and U.S. patent application Ser. No. 10/844,475, entitled "TEMPLATE BASED AV/VA INTERVAL COMPARISON FOR THE DISCRIMINATION OF CARDIAC ARRHYTHMIAS," filed on May 12, 2004, both assigned to Cardiac Pacemakers, Inc., which are hereby incorporated herein by reference in their entirety.

If the detected tachyarrhythmia episode is classified as a type of tachyarrhythmia for which the cardioversion/defibrillation therapy is to be delivered, tachyarrhythmia reconfirmation module 458 starts a tachyarrhythmia reconfirmation window immediately before the scheduled delivery of a cardioversion/defibrillation pulse. If the heart beats detected during the tachyarrhythmia reconfirmation window include at least a minimum number or percentage of fast beats, a reconfirmation of tachyarrhythmia is declared (the tachyarrhythmia reconfirmation window is satisfied). Otherwise, the delivery the cardioversion/defibrillation therapy is withheld.

Inhibitory event detector 430 is a specific embodiment of inhibitory event detector 230 and detects the predetermined type inhibitory event that indicates the need to inhibit the delivery of the cardioversion/defibrillation therapy. In one embodiment, if inhibitory event detector 430 detects an inhibitory event during the tachyarrhythmia verification period, tachyarrhythmia detection module 452 restarts the tachyarrhythmia detection window, thereby restating the tachyarrhythmia detection and classification process. In another embodiment, if inhibitory event detector 430 detects an inhibitory event during the tachyarrhythmia verification period, tachyarrhythmia verification module 454 extends the tachyarrhythmia verification period, thereby extending the tachyarrhythmia detection and classification process, until after the inhibitory event is no longer detected while the verification window remains satisfied. If the inhibitory event detector 430 detects an inhibitory event during the tachyarrhythmia reconfirmation window, tachyarrhythmia reconfirmation module 458 restarts or extends the tachyarrhythmia reconfirmation window, thereby withholding the delivery the cardioversion/defibrillation therapy unless and until the inhibitory event is no longer detected. In one embodiment, as illustrated in FIG. 4, inhibitory event detector 430 includes an arrhythmia pattern detector 460 and a slow beat analyzer 462. In various embodiments, inhibitory event detector 430 includes any one, or both, of arrhythmia pattern detector 460 and slow beat analyzer 462.

Arrhythmia pattern detector 460 detects a predetermined type arrhythmia pattern and indicates the detection of the inhibitory event when the predetermined type arrhythmia pattern is detected. The predetermined type arrhythmia pattern includes repetitive beat sequences each including a first number (F) of fast beats followed by a second number (S) of slow beats, and the numbers of F to S (F/S) fall into one or more predetermined fast-slow beat patterns. The predetermined fast-slow beat patterns typically include (i) three or more fast beats followed by one slow beats ($F \geq 3$, $S=1$), (ii) four or more fast beats followed by two slow beats ($F \geq 4$, $S=2$), (iii) eight or more fast beats followed by three slow beats ($F \geq 8$, $S=3$), and (iv) eight or more fast beats followed by four slow beats ($F \geq 8$, $S=4$). Thus, in certain examples, given the number of the slow beats that follows the fast beats, the ratio of F:S is equal to or greater than (i) 3:1, (ii) 4:2, (iii) 8:3, and (iv) 8:4. If the number of the consecutively detected slow beats exceeds four, the verification window is deemed not satisfied, and the tachyarrhythmia detection and classification process is terminated without delivering the cardioversion/defibrillation therapy because the detected tachyarrhythmia episode is considered non-sustaining. The repetitive beat sequences may include beat sequences having different fast-slow beat patterns with each of the fast-slow beat patterns belonging to one of the predetermined fast-slow beat patterns. Specific examples of the predetermined type arrhythmia patterns are further discussed below with reference to FIG. 6.

Slow beat analyzer 462 analyzes each of the slow beats to detect normal slow beats and indicates the detection of the predetermined type inhibitory event when one or more normal slow beats are detected. The one or more normal slow beats constitute an indication of a normal cardiac rhythm or an arrhythmia for which the cardioversion/defibrillation therapy is not necessary or applicable. In one embodiment, slow beat analyzer 462 analyzes a correlation between a slow beat morphology and a template beat morphology and declare a detection of the normal slow beat when the slow beat morphology and the template beat morphology substantially correlate. The slow beat morphology is the morphology of the cardiac signal sensed during each of the detected slow beats. The template beat morphology is the morphology of the cardiac signal sensed during a template heart beat of the normal cardiac rhythm or the arrhythmia for which the cardioversion/defibrillation therapy is not necessary or applicable. In one embodiment, in which controller 426 controls ventricular cardioversion/defibrillation, the template heart beat represents a heart beat of NSR or SVT. In addition, a paced heart beat is considered as a normal slow beat without the need of going through the correlation analysis.

Defibrillation controller 432 is a specific embodiment of defibrillation controller 232 and controls the preparation and delivery of the cardioversion/defibrillation pulses. Defibrillation controller 432 includes a defibrillation preparation controller 464 and a defibrillation delivery controller 466. Defibrillation preparation controller 464 starts a therapy preparation process when the detected tachyarrhythmia is classified as a tachyarrhythmia for which the cardioversion/ defibrillation therapy is to be delivered. In one embodiment, the ventricular cardioversion/defibrillation therapy is prepared when the detected tachyarrhythmia is classified as a VT originating from the ventricles. The therapy preparation process includes charging of a capacitor in which the energy of the cardioversion/defibrillation pulse is stored before the delivery of the pulse. Tachyarrhythmia reconfirmation module 458 starts the tachyarrhythmia reconfirmation window when the therapy preparation process is completed. If the reconfirmation of tachyarrhythmia is declared, defibrillation delivery controller 466 causes the delivery of the cardioversion/defibrillation pulse.

Figure 5:
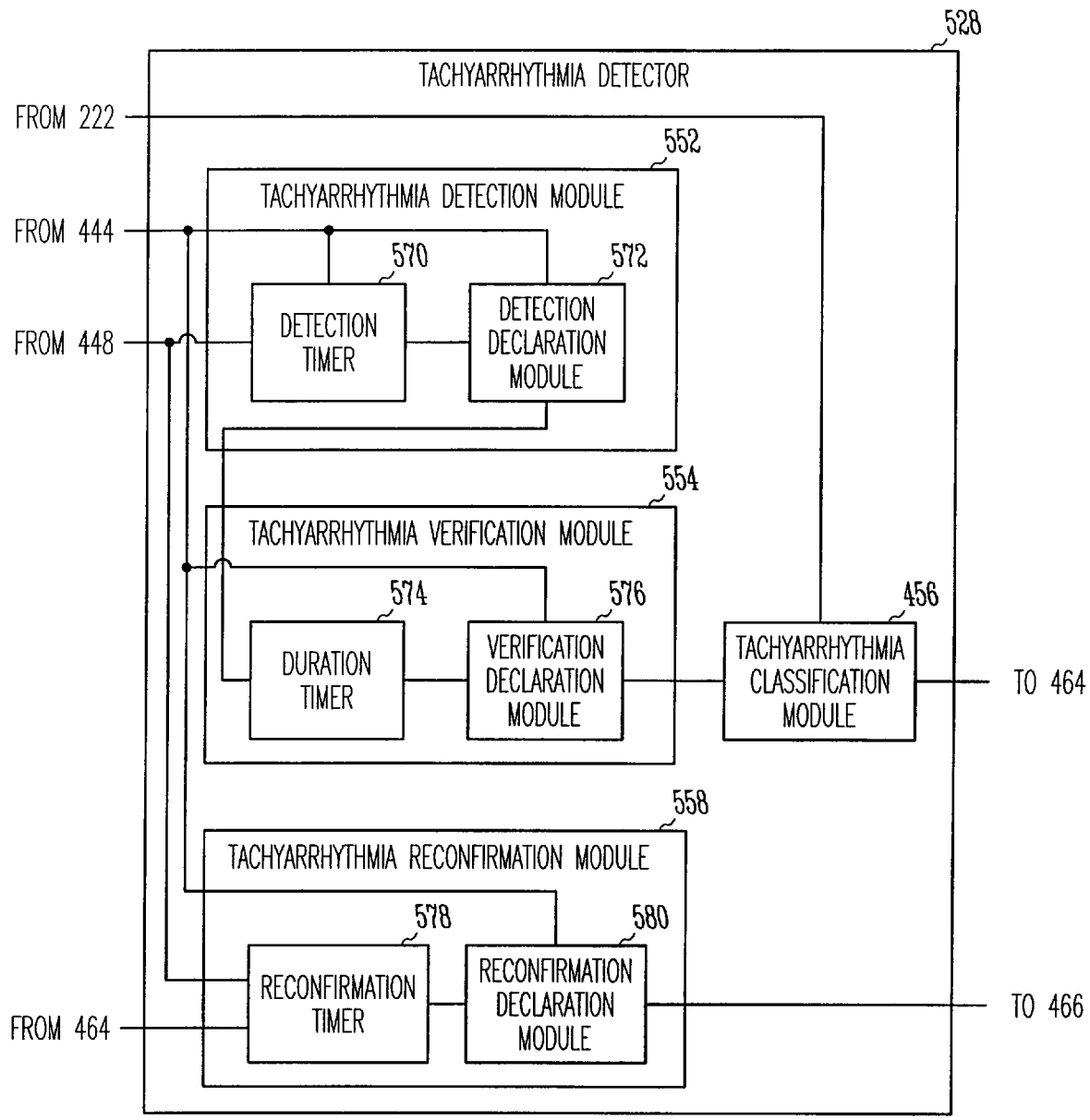
FIG. 5 is a block diagram illustrating an embodiment of a tachyarrhythmia detector of the controller.

FIG. 5 is a block diagram illustrating an embodiment of a tachyarrhythmia detector 528, which is a specific embodiment of tachyarrhythmia detector 428. Tachyarrhythmia detector 528 includes a tachyarrhythmia detection module 552, a tachyarrhythmia verification module 554, tachyarrhythmia classification module 456, and a tachyarrhythmia reconfirmation module 558.

Tachyarrhythmia detection module 552 is a specific embodiment of tachyarrhythmia detection module 452 and includes a detection timer 570 and a detection declaration module 572. Tachyarrhythmia detection module 552 detects the predetermined type initiation event. Detection timer 570 starts the tachyarrhythmia detection window in response to the detection of the predetermined type initiation event. In one embodiment, detection timer 570 also restarts the tachyarrhythmia detection window in response to the detection of the predetermined type inhibitory event. The tachyarrhythmia detection window includes a predetermined number of consecutively detected beats. In one embodiment, the predetermined type initiation event includes the detection of three consecutive fast beats. Detection declaration module 572 declares the detection of tachyarrhythmia (the tachyarrhythmia detection window satisfied) when the number of fast beats detected during the tachyarrhythmia detection window equals or exceeds a predetermined detection threshold. In one embodiment, the tachyarrhythmia detection window includes ten consecutively detected heart beats, and tachyarrhythmia detector 528 declares a detection of tachyarrhythmia when at least eight fast beats are detected during the tachyarrhythmia detection window.

Tachyarrhythmia verification module 554 is a specific embodiment of tachyarrhythmia verification module 454 and includes a duration timer 574 and a verification declaration module 576. Duration timer 574 starts the tachyarrhythmia verification duration when the detection of tachyarrhythmia is declared by detection declaration module 572 and times the tachyarrhythmia verification duration. In one embodiment, duration timer 574 extends the tachyarrhythmia verification duration in response to the detection of the predetermined type inhibitory event. Verification declaration module 576 declares the verification of tachyarrhythmia (the tachyarrhythmia verification duration satisfied) when the number of fast beats detected during a verification window equals or exceeds a predetermined verification threshold. The verification of tachyarrhythmia indicates that the tachyarrhythmia sustains throughout the tachyarrhythmia verification duration. The verification window is a moving window ending with each heart beat detected during the tachyarrhythmia verification duration. The moving verification window includes a predetermined number of consecutively detected heart beats. In one embodiment, the verification window includes ten consecutively detected heart beats, and verification declaration module 576 declares the verification of the tachyarrhythmia when at least six fast beats are detected during the moving verification window throughout the tachyarrhythmia verification duration. In one embodiment, duration timer 574 extends the tachyarrhythmia verification duration to include an additional beat if the last detected beat of the tachyarrhythmia verification duration is classified as a slow beat.

Tachyarrhythmia reconfirmation module 558 is a specific embodiment of tachyarrhythmia reconfirmation module 458 and includes a reconfirmation timer 578 and a reconfirmation declaration module 580. Reconfirmation timer 578 starts the tachyarrhythmia reconfirmation window when the therapy preparation process is completed. The tachyarrhythmia reconfirmation window includes a predetermined number of consecutively detected beats. If the predetermined type inhibitory event is detected during the tachyarrhythmia reconfirmation window, reconfirmation timer 578 restarts or extends the tachyarrhythmia reconfirmation window. The tachyarrhythmia reconfirmation window is restarted or extended as long as the inhibitory event is being detected. Reconfirmation declaration module 580 declares the reconfirmation of tachyarrhythmia (the tachyarrhythmia reconfirmation window satisfied) when the number of fast beats detected during the tachyarrhythmia reconfirmation window equals or exceeds a predetermined reconfirmation threshold. In one embodiment, the tachyarrhythmia reconfirmation window includes three consecutively detected beats, and reconfirmation declaration module 580 declares the reconfirmation of tachyarrhythmia when at least two fast beats are detected during the tachyarrhythmia reconfirmation window.

FIG. 6 is an illustration of arrhythmia patterns I-IV each being an example of a predetermined type inhibitory event detectable by arrhythmia pattern detector 460. Each of the patterns I-IV illustrates a scenario that both the detection of tachyarrhythmia and the verification of tachyarrhythmia would be declared if the inhibitory event had not been detected. The tachyarrhythmia detection window includes ten consecutively detected heart beats and is satisfied if eight out of the ten beats are fast beats. The moving verification window during the tachyarrhythmia verification duration includes ten consecutively detected heart beats and is satisfied if six out of the ten beats are fast beats.

Pattern I (P.I) starts with a 3:1 fast-slow pattern (repetitive sequence of three fast beats followed by one slow beats) and changes to a 2:1 fast-slow pattern at beat number 13. Pattern II (P.II) starts with a 4:2 fast-slow pattern and changes to a 2:1 fast-slow pattern at beat number 13. Pattern III (P.III) starts with an 8:3 fast-slow pattern and changes to a 3:1 fast-slow pattern at beat number 12. Pattern IV (P.IV) starts with an 8:4 fast-slow pattern and changes to a 6:4 fast-slow pattern at beat number 13. In each of Patterns I-IV, the detection of beats number 1-3, which are three consecutive fast beats, starts the tachyarrhythmia detection window. Beats number 1-10 includes eight fast beats and two slow beats, thereby satisfying the tachyarrhythmia detection window and causes the tachyarrhythmia verification duration to be started at beat number 11. Each moving verification window during the tachyarrhythmia verification duration as shown in FIG. 6 includes at least six fast beats (i.e., any ten consecutively detected heart beats during the tachyarrhythmia verification duration include at least six fast beats), thereby satisfying the verification window. However, each of Patterns I-IV is an arrhythmia pattern for which the cardioversion/defibrillation therapy is deemed unnecessary or inapplicable. Thus, such patterns are included as the predetermined type inhibitory events. For illustration purposes, Patterns I-IV are each an example of predetermined fast-slow beat patterns detectable by arrhythmia pattern detector 460, as discussed above with reference to FIG. 4.

Figure 7A:
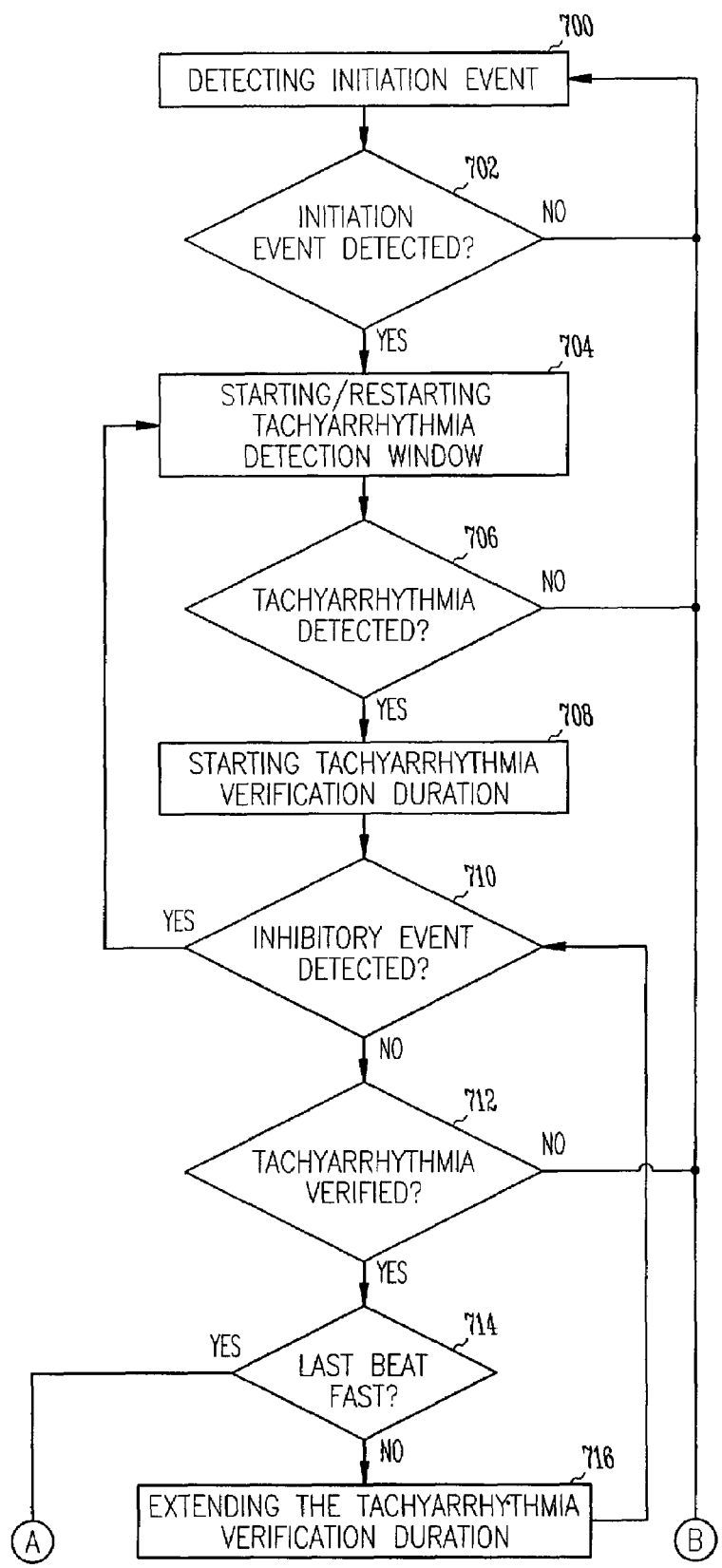
FIGS. 7A-B are a flow chart illustrating an embodiment of a method for controlling the delivery of a cardioversion/defibrillation therapy.
Figure 7B:
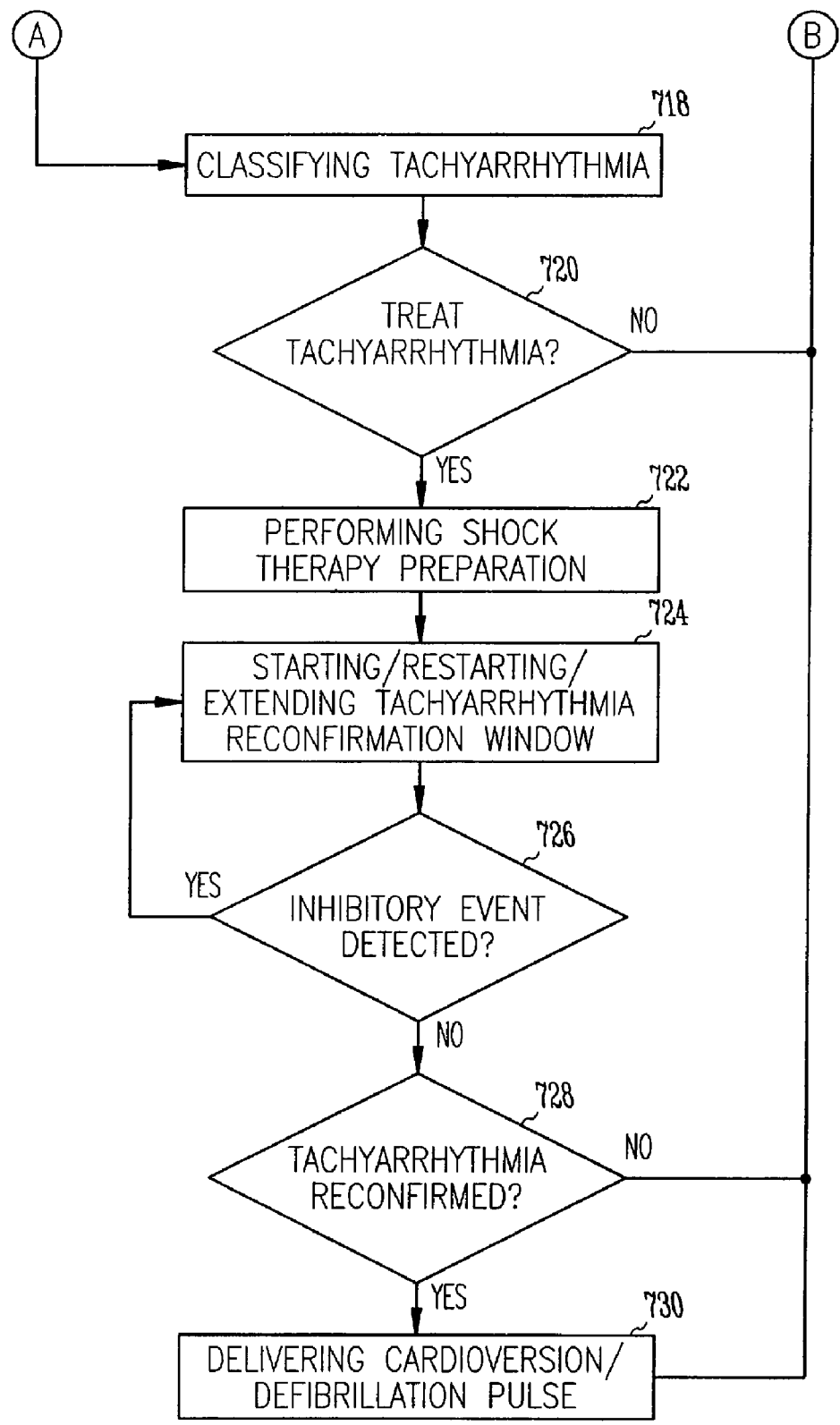

FIGS. 7A and 7B include a flow chart illustrating an embodiment of a method for controlling the delivery of a cardioversion/defibrillation therapy. In one embodiment, the method is performed by system 100, including the various embodiments of its components discussed above with reference to FIGS. 1-5.

An initiation event is being detected from a cardiac signal at 700. The initiation event indicates a possible onset of a tachyarrhythmia episode that warrants the initiation of a tachyarrhythmia detection and classification process. The tachyarrhythmia detection and classification process determines whether a cardioversion/defibrillation therapy is to be delivered. In one embodiment, the initiation event is the detection of three consecutive fast beats. In one embodiment, the cardiac signal is a ventricular electrogram. The initiation event indicates a possible onset of a VT episode. The tachyarrhythmia detection and classification process determines whether VT episode is a true VT episode (i.e., a tachyarrhythmia of ventricular origin) and sustains. The cardioversion/defibrillation therapy includes the delivery of one or more ventricular cardioversion/defibrillation pulses.

If the initiation event is detected at 702, a tachyarrhythmia detection window is started at 704. The tachyarrhythmia detection window includes a predetermined number of consecutively detected heart beats. A detection of tachyarrhythmia (the satisfaction of the tachyarrhythmia detection window) is declared at the end of the tachyarrhythmia detection window if the number of fast beats detected during the tachyarrhythmia detection window equals or exceeds a predetermined detection threshold. In one embodiment of VT detection, a detection of VT is declared at the end of the tachyarrhythmia detection window when at least eight fast beats are detected during the tachyarrhythmia detection window, which includes ten consecutively detected heart beats.

If the detection of tachyarrhythmia is not declared at 706, the tachyarrhythmia detection and classification process is terminated without delivering the cardioversion/defibrillation therapy. If the detection of tachyarrhythmia is declared at the end of the tachyarrhythmia detection window at 706, a tachyarrhythmia verification duration is started at 708. A verification of tachyarrhythmia (the satisfaction of the tachyarrhythmia verification duration) is declared at the end of the tachyarrhythmia verification duration if a number of fast beats detected during a moving verification window equals or exceeds a predetermined verification threshold throughout the tachyarrhythmia verification duration. The moving verification window is a moving window ending with each heart beat detected during the tachyarrhythmia verification duration and includes a predetermined number of consecutively detected heart beats. In one embodiment of VT verification, the moving verification window is satisfied if at least six fast beats are detected during the moving verification window, which includes ten consecutively detected heart beats.

In one embodiment, as illustrated in FIG. 7, if a predetermined type inhibitory event is detected during the tachyarrhythmia verification duration at 710, the tachyarrhythmia detection window is restarted at 704. The predetermined type inhibitory event indicates that the cardioversion/defibrillation therapy is unnecessary or inapplicable. Examples of the predetermined type inhibitory event include (i) a predetermined type arrhythmia pattern indicative of an arrhythmia not to be treated by the cardioversion/defibrillation therapy and (2) one or more "normal slow beats" indicative of a non-sustaining tachyarrhythmia episode. The predetermined type arrhythmia pattern includes repetitive beat sequences each including a first number (F) of fast beats followed by a second number (S) of slow beats, wherein the numbers F and S fall into one or more predetermined patterns. In one embodiment, the inhibitory event is detected if (i) $F \geq 3$, $S=1$; (ii) $F \geq 4$, $S=2$; (iii) $F \geq 8$, $S=3$; and (iv) $F \geq 8$, $S=4$. The predetermined type arrhythmia pattern also include repetitive beat sequences that include beat sequences having different combination of F and S as long as each of the combinations of F and S falls into one of the predetermined patterns. Each normal slow beat is detected by analyzing a correlation between a slow beat morphology and a template beat morphology. The slow beat morphology is the morphology of the cardiac signal sensed during each of the detected slow beats. The template beat morphology is representative of a morphology of the cardiac signal detected during a "normal heart beat". In one embodiment of VT verification, the normal heart beat represents a heart beat of NSR or SVT. A normal slow beat is detected when the slow beat morphology and the template beat morphology substantially correlate.

If the verification of tachyarrhythmia is not declared at the end of the tachyarrhythmia verification duration at 712 because the moving verification window is not satisfied at any time during the tachyarrhythmia verification duration, the tachyarrhythmia detection and classification process is terminated without delivering the cardioversion/defibrillation therapy. If the verification of tachyarrhythmia is declared at the end of the tachyarrhythmia verification duration at 712, and if the last heart beat during the tachyarrhythmia verification duration is classified as a fast beat at 714, the tachyarrhythmia is classified at 718. If the verification of tachyarrhythmia is declared at the end of the tachyarrhythmia verification duration at 712, but the last heart beat during the tachyarrhythmia verification duration is not classified as a fast beat at 714, the tachyarrhythmia verification duration is extended at 716. In one embodiment, if the predetermined type inhibitory event is detected during the tachyarrhythmia verification duration at 710, the tachyarrhythmia verification duration is extended until after the predetermined type inhibitory event is no longer detected. The detected tachyarrhythmia episode is classified by its origin and/or type at 718. In one embodiment, the detected tachyarrhythmia episode is classified as one of VT and SVT by comparing the morphology of the cardiac signal sensed during the detected tachyarrhythmia episode to a template morphology associated with a known cardiac rhythm such as NSR. Specific examples of tachyarrhythmia classification are discussed in U.S. patent application Ser. No. 11/038,996 and U.S. patent application Ser. No. 10/844,475.

If the tachyarrhythmia is classified as a type for which the ventricular cardioversion/defibrillation therapy is unnecessary or inapplicable at 720, the tachyarrhythmia detection and classification process is terminated without delivering the cardioversion/defibrillation therapy. If the tachyarrhythmia is classified as a type that needs to be treated by a cardioversion/defibrillation therapy at 720, a cardioversion/defibrillation therapy preparation is performed at 722. The cardioversion/defibrillation therapy preparation includes charging a capacitor in which the energy of the cardioversion/defibrillation pulse is stored before the delivery. The capacitor is to be charged to a level associated with the specified energy level of the cardioversion/defibrillation pulse.

When the cardioversion/defibrillation therapy preparation is completed (i.e., the cardioversion/defibrillation pulse is ready to be delivered), a tachyarrhythmia reconfirmation window is started at 724. The tachyarrhythmia reconfirmation window includes a predetermined number of consecutively detected beats. The reconfirmation of tachyarrhythmia (satisfaction of the tachyarrhythmia reconfirmation window) is declared if a number of fast beats detected during the tachyarrhythmia reconfirmation window equals or exceeds a predetermined reconfirmation threshold. In one embodiment of VT reconfirmation, the reconfirmation of VT is declared when at least two fast beats are detected during the tachyarrhythmia reconfirmation window, which includes three consecutively detected beats.

If the predetermined type inhibitory event is detected during the tachyarrhythmia reconfirmation window at 726, the tachyarrhythmia reconfirmation window is restarted or extended at 724, such that the reconfirmation of tachyarrhythmia is not declared unless and until the predetermined type inhibitory event is no longer detected while the tachyarrhythmia episode still sustains. That is, if the predetermined type inhibitory event is detected during the tachyarrhythmia reconfirmation window, the delivery of the cardioversion/defibrillation pulse is withheld unless and until the predetermined type inhibitory event is no longer detected while the tachyarrhythmia episode still sustains. If the reconfirmation of tachyarrhythmia is not declared at 728, the tachyarrhythmia detection and classification process is terminated without delivering the cardioversion/defibrillation therapy. If the reconfirmation of tachyarrhythmia is declared at 728, the cardioversion/defibrillation pulse is delivered at 730.

It is to be understood that the above detailed description is intended to be illustrative, and not restrictive. Other embodiments will be apparent to those of skill in the art upon reading and understanding the above description. The scope of the invention should, therefore, be determined with reference to the appended claims, along with the full scope of equivalents to which such claims are entitled.

What is claimed is:

1. An implantable medical device, comprising:
    a sensing circuit to sense a cardiac signal; and
    a controller adapted to control a delivery of an anti-tachyarrhythmia therapy, the controller including:
        a tachyarrhythmia detector coupled to the sensing circuit, the tachyarrhythmia detector adapted to detect a predetermined type initiation event indicative of a tachyarrhythmia episode from the cardiac signal, to start a tachyarrhythmia detection and classification process in response to the detection of the predetermined type initiation event, and to restart or extend the tachyarrhythmia detection and classification process in response to a detection of a predetermined type inhibitory event, the tachyarrhythmia detection and classification process determining whether the tachyarrhythmia episode sustains and is to be treated by the delivery of the anti-tachyarrhythmia therapy;
        a beat detector coupled to the sensing circuit, the beat detector adapted to detect heart beats from the cardiac signal;
        a heart rate detector coupled to the beat detector, the heart rate detector adapted to detect a heart rate associated with each of the detected heart beats;
        a beat classifier coupled to the heart rate detector, the beat classifier adapted to classify each of the detected heart beat as one of a fast beat and a slow beat using the heart rate associated with the each of the detected heart beats, the fast beat being a detected heart beat associated with a heart rate within a tachyarrhythmia detection zone, the slow beat being one of a detected heart beat associated with a heart rate below the tachyarrhythmia detection zone and a paced heart beat; and
        an inhibitory event detector coupled to the tachyarrhythmia detector and the beat classifier, the inhibitory event detector adapted to detect the predetermined type inhibitory event from the cardiac signal, the predetermined type inhibitory event indicative of a need to inhibit the delivery of the anti-tachyarrhythmia therapy, the inhibitory event detector comprises an arrhythmia pattern detector adapted to detect a predetermined type arrhythmia pattern and indicate the detection of the predetermined type inhibitory event when the predetermined type arrhythmia pattern is detected, the predetermined type arrhythmia pattern including repetitive beat sequences each including a first number (F) of the fast beats followed by a second number (S) of the slow beats, wherein in the numbers F and S fall into one or more predetermined patterns.

2. The implantable medical device of claim 1, further comprising a defibrillation circuit to deliver cardioversion/defibrillation pulses, wherein the controller comprises a defibrillation controller coupled to the tachyarrhythmia detector and the defibrillation circuit, the defibrillation controller adapted to control the delivery of the cardioversion/defibrillation pulses, and wherein the delivery of the anti-tachyarrhythmia therapy comprises a delivery of one or more of the cardioversion/defibrillation pulses.

3. The implantable medical device of claim 1, further comprising a pacing circuit to deliver pacing pulses, wherein the controller comprises a pacing controller coupled to the tachyarrhythmia detector and the pacing circuit, the pacing controller adapted to control the delivery of the pacing pulses according to an anti-tachyarrhythmia pacing (ATP) algorithm, and wherein the delivery of the anti-tachyarrhythmia therapy comprises a delivery of one or more of the pacing pulses.

4. The implantable medical device of claim 1, wherein the arrhythmia pattern detector is adapted to detect predetermined type arrhythmia patterns in which:
    F is equal to or greater than 3 if S is equal to 1;
    F is equal to or greater than 4 if S is equal to 2;
    F is equal to or greater than 8 if S is equal to 3; and
    F is equal to or greater than 8 if S is equal to 4.

5. The implantable medical device of claim 1, wherein the repetitive beat sequences include at least two beat sequences having different ratios of F to S each falling into one of a plurality of predetermined patterns.

6. The implantable medical device of claim 1, wherein the inhibitory event detector comprises a slow beat analyzer to analyze each of the slow beats to detect normal slow beats and indicate the detection of the predetermined type inhibitory event when one or more of the normal slow beats are detected.

7. The implantable medical device of claim 6, wherein the inhibitory event detector is adapted to indicate the detection of the predetermined type inhibitory event when one or more paced beats are detected.

8. The implantable medical device of claim 6, wherein the inhibitory event detector comprises a correlation analyzer to analyze a correlation between a slow beat morphology and a template beat morphology and declare a detection of the normal slow beat when the slow beat morphology and the template beat morphology substantially correlate, the slow beat morphology being a morphology of the cardiac signal sensed during one of the detected slow beats.

9. The implantable medical device of claim 1, wherein the tachyarrhythmia detector comprises a tachyarrhythmia detection module including:
    a detection timer adapted to start a tachyarrhythmia detection window in response to the detection of the predetermined type initiation event, the tachyarrhythmia detection window including a predetermined number of consecutively detected beats; and
    a detection declaration module adapted to declare a detection of tachyarrhythmia when a number of the fast beats detected during the tachyarrhythmia detection window equals or exceeds a predetermined detection threshold.

10. The implantable medical device of claim 9, wherein the detection timer is adapted to restart the tachyarrhythmia detection window in response to the detection of the predetermined type inhibitory event.

11. The implantable medical device of claim 9, wherein the tachyarrhythmia detector comprises a tachyarrhythmia verification module coupled to the tachyarrhythmia detection module, the tachyarrhythmia verification module including:
   a duration timer adapted to start a tachyarrhythmia verification duration when the detection of tachyarrhythmia is declared and to time the tachyarrhythmia verification duration; and
   a verification declaration module adapted to declare that the tachyarrhythmia episode sustains when a number of the fast beats detected during a verification window equals or exceeds a predetermined verification threshold, the verification window being a moving window ending with each heart beat detected during the tachyarrhythmia verification duration and including a predetermined number of consecutively detected heart beats.

12. The implantable medical device of claim 11, wherein the duration timer is adapted to extend the tachyarrhythmia verification duration in response to the detection of the predetermined type inhibitory event.

13. The implantable medical device of claim 11, wherein the tachyarrhythmia detector further comprises a tachyarrhythmia classification module adapted to classify the tachyarrhythmia episode when the tachyarrhythmia verification duration expires.

14. The implantable medical device of claim 13, wherein the tachyarrhythmia detector further comprises a tachyarrhythmia reconfirmation module including:
   a reconfirmation timer adapted to start a tachyarrhythmia reconfirmation window when a preparation for the delivery of the anti-tachyarrhythmia therapy is completed, the tachyarrhythmia reconfirmation window including a predetermined number of consecutively detected beats; and
   a reconfirmation declaration module adapted to declare a reconfirmation of tachyarrhythmia when a number of the fast beats detected during the tachyarrhythmia reconfirmation window equals or exceeds a predetermined reconfirmation threshold and the predetermined type inhibitory event is not detected during the tachyarrhythmia reconfirmation window.

15. The implantable medical device of claim 14, wherein the reconfirmation timer is adapted to restart the tachyarrhythmia reconfirmation window if the predetermined type inhibitory event is detected during the tachyarrhythmia reconfirmation window.

16. The implantable medical device of claim 14, further comprising a defibrillation circuit adapted to deliver ventricular cardioversion/defibrillation pulses, wherein the controller comprises a defibrillation controller adapted to control the delivery of the ventricular cardioversion/defibrillation pulses, and wherein:
   the sensing circuit is adapted to sense a ventricular electrogram;
   the beat detector is adapted to detect ventricular events as the heart beats; from the ventricular electrogram;
   the tachyarrhythmia detector is adapted to declare a detection of ventricular tachyarrhythmia (VT) when at least eight fast beats are detected during the tachyarrhythmia detection window, wherein the tachyarrhythmia detection window includes ten consecutively detected heart beats;
   the verification declaration module is adapted to declare that the VT sustains when at least six fast beats are detected during the verification window, wherein the verification window includes ten consecutively detected heart beats;
   the tachyarrhythmia classification module is adapted to classify the detected tachyarrhythmia as one of VT and supraventricular tachyarrhythmia (SVT); and
   the tachyarrhythmia reconfirmation module is adapted to declare a reconfirmation of tachyarrhythmia when at least two fast beats are detected during the tachyarrhythmia reconfirmation window, wherein the tachyarrhythmia reconfirmation window includes three consecutively detected beats.

17. The implantable medical device of claim 16, wherein the defibrillation controller comprises:
   a defibrillation preparation controller adapted to start the preparation for the delivery of one or more of the cardioversion/defibrillation pulses when the detected tachyarrhythmia is classified; and
   a defibrillation delivery controller adapted to cause a delivery of one or more of the cardioversion/defibrillation pulses when the reconfirmation of tachyarrhythmia is declared.

18. A method for operating an implantable medical device, the method comprising:
   sensing a cardiac signal;
   detecting heart beats from the cardiac signal;
   detecting a heart rate associated with each of the detected heart beats;
   classifying each of the detected heart beat as one of a fast beat and a slow beat using the heart rate associated with the each of the detected heart beat, the fast beat being a detected heart beat associated with a heart rate within a tachyarrhythmia detection zone, the slow beat being one of a detected heart beat associated with a heart rate below the tachyarrhythmia detection zone and a paced heart beat;
   detecting a predetermined type initiation event indicative of a tachyarrhythmia episode from the cardiac signal;
   starting a tachyarrhythmia detection and classification process when the predetermined type initiation event is detected;
   detecting a predetermined type inhibitory event from the cardiac signal, the predetermined type inhibitory event indicative of a need to inhibit a delivery of an anti-tachyarrhythmia therapy, wherein the detecting the predetermined type inhibitory event includes:
      detecting a predetermined type arrhythmia pattern including repetitive beat sequences each including a first number (F) of the fast beats followed by a second number (S) of the slow beats, wherein in the numbers F and S fall into one or more determined patterns; and
      indicating the detection of the predetermined type inhibitory event when the predetermined arrhythmia pattern is detected; and
   restarting or extending the tachyarrhythmia detection and classification process when the predetermined type inhibitory event is detected.

19. The method of claim 18, further comprising determining whether the tachyarrhythmia episode sustains and is treatable by the delivery of the anti-tachyarrhythmia; therapy during the tachyarrhythmia detection and classification process.

20. The method of claim 19, wherein the delivery of the anti-tachyarrhythmia therapy comprises a delivery of one or more cardioversion/defibrillation pulses.

21. The method of claim 19, wherein the delivery of the anti-tachyarrhythmia therapy comprises a delivery of one or more pacing pulses according to an anti-tachyarrhythmia pacing (ATP) algorithm.

22. The method of claim 18, wherein indicating the detection of the predetermined type inhibitory event when the predetermined type arrhythmia pattern is detected comprises indicating the detection of the predetermined type inhibitory event when F is equal to or greater than 3 if S is equal to 1, when F is equal to or greater than 4 if S is equal to 2, when F is equal to or greater than 8 if S is equal to 3, and when F is equal to or greater than 8 if S is equal to 4.

23. The method of claim 18, wherein the repetitive beat sequences include at least two beat sequences having different ratios of F to S each falling into one of a plurality of predetermined patterns.

24. The method of claim 18, wherein detecting the predetermined type inhibitory event comprises:
analyzing each of the slow beats to detect normal slow beats; and
indicating the detection of the predetermined type inhibitory event when one or more of the normal slow beats are detected.

25. The method of claim 24, wherein detecting the predetermined type inhibitory event further comprises indicating the detection of the predetermined type inhibitory event when one or more paced beats are detected.

26. The method of claim 24, wherein analyzing the each of the slow beats to detect normal slow beats comprises:
analyzing a correlation between a slow beat morphology and a template beat morphology, the slow beat morphology being a morphology of the cardiac signal sensed during the each of the detected slow beats; and
declaring a detection of the normal slow beat when the slow beat morphology and the template beat morphology substantially correlate.

27. The method of claim 18, wherein determining whether the tachyarrhythmia episode sustains and is treatable by the delivery of the anti-tachyarrhythmia therapy comprises:
starting a tachyarrhythmia detection window in response to the predetermined type initiation event, the tachyarrhythmia detection window including a predetermined number of consecutively detected beats; and
declaring a detection of tachyarrhythmia when a number of the fast beats detected during the tachyarrhythmia detection window equals or exceeds a predetermined detection threshold.

28. The method of claim 27, further comprising restarting the tachyarrhythmia detection window in response to the detection of the predetermined type inhibitory event.

29. The method of claim 27, wherein determining whether the tachyarrhythmia episode sustains and is treatable by the delivery of the anti-tachyarrhythmia therapy further comprises:
starting a tachyarrhythmia verification duration when the detection of tachyarrhythmia is declared; and
declaring a verification of tachyarrhythmia if a number of the fast beats detected during a; verification window equals or exceeds a predetermined verification threshold throughout the tachyarrhythmia verification duration, the verification window being a moving window ending with each heart beat detected during the tachyarrhythmia verification duration and including a; predetermined number of consecutively detected heart beats.

30. The method of claim 29, further comprising extending the tachyarrhythmia verification duration in response to the detection of the predetermined type inhibitory event.

31. The method of claim 29, wherein determining whether the tachyarrhythmia episode sustains and is treatable by the delivery of the anti-tachyarrhythmia therapy further comprises classifying the detected tachyarrhythmia when the verification of tachyarrhythmia is declared, wherein the delivery of the anti-tachyarrhythmia therapy comprises a delivery of a; cardioversion/defibrillation pulse, and further comprising starting a therapy preparation process if the detected tachyarrhythmia classified as a treatable tachyarrhythmia.

32. The method of claim 31, further comprising:
starting a tachyarrhythmia reconfirmation window when the therapy preparation process is completed, the tachyarrhythmia reconfirmation window including a predetermined number of consecutively detected beats;
declaring a reconfirmation of tachyarrhythmia when a number of the fast beats detected; during the tachyarrhythmia reconfirmation window equals or exceeds a predetermined; reconfirmation threshold and the predetermined type inhibitory event is not detected during the tachyarrhythmia reconfirmation window; and
delivering the cardioversion/defibrillation pulse when the reconfirmation of tachyarrhythmia is declared.

33. The method of claim 32, further comprising restarting the tachyarrhythmia reconfirmation window if the predetermined type inhibitory event is detected during the tachyarrhythmia reconfirmation window.

34. The method of claim 32, wherein:
sensing the cardiac signal comprises sensing a ventricular electrogram;
detecting the heart beats comprises detecting ventricular events as the heart beats from the ventricular electrogram;
starting the tachyarrhythmia detection and classification process if the predetermined type initiation event is detected comprises starting a ventricular tachyarrhythmia (VT) detection and classification process if three consecutively detected heart beats are classified as the fast beats;
declaring the detection of tachyarrhythmia comprises declaring a detection of VT when at least eight fast beats are detected during the tachyarrhythmia detection window, wherein the tachyarrhythmia detection window includes ten consecutively detected heart beats;
declaring that the tachyarrhythmia sustains comprises declaring that the VT sustains when at least six fast beats are detected during the verification window, wherein the verification window includes ten consecutively detected heart beats;
classifying the detected VT comprises confirming the detection of VT by discriminating between VT and supraventricular tachyarrhythmia (SVT); and
declaring the reconfirmation of tachyarrhythmia comprises a reconfirmation of VT when at least two fast beats are detected during the tachyarrhythmia reconfirmation window, wherein the tachyarrhythmia reconfirmation window includes three consecutively detected beats.

* * * * *

UNITED STATES PATENT AND TRADEMARK OFFICE
CERTIFICATE OF CORRECTION

| | |
|---|---|
| PATENT NO. | : 7,689,282 B2 |
| APPLICATION NO. | : 11/424743 |
| DATED | : March 30, 2010 |
| INVENTOR(S) | : Yunlong Zhang et al. |

It is certified that error appears in the above-identified patent and that said Letters Patent is hereby corrected as shown below:

In column 17, line 64, in Claim 16, delete "beats;" and insert -- beats --, therefor.

In column 18, line 57, in Claim 18, delete "determined" and insert -- predetermined --, therefor.

In column 18, line 59, in Claim 18, after "predetermined" insert -- type --.

In column 19, line 62, in Claim 29, delete "a;" and insert -- a --, therefor.

In column 20, line 2, in Claim 29, delete "a;" and insert -- a --, therefor.

In column 20, line 13, in Claim 31, delete "a;" and insert -- a --, therefor.

In column 20, line 23, in Claim 32, delete "detected;" and insert -- detected --, therefor.

In column 20, line 25, in Claim 32, delete "predetermined;" and insert -- predetermined --, therefor.

Signed and Sealed this

Twenty-ninth Day of June, 2010

David J. Kappos
*Director of the United States Patent and Trademark Office*